US00PP36243P2

(12) United States Plant Patent
Nilson

(10) Patent No.: US PP36,243 P2
(45) Date of Patent: Nov. 5, 2024

(54) ***X OREDENIA* PLANT NAMED 'Fusion of Fire'**

(50) Latin Name: ***Oresitrophe* x *Mukdenia* hybrid (x *Oredenia)***
Varietal Denomination: Fusion of Fire

(71) Applicant: Johan G. Nilson, Gothenburg (SE)

(72) Inventor: Johan G. Nilson, Gothenburg (SE)

( * ) Notice: Subject to any disclaimer, the term of this patent is extended or adjusted under 35 U.S.C. 154(b) by 0 days.

(21) Appl. No.: 18/445,504

(22) Filed: Sep. 6, 2023

(51) Int. Cl.
*A01H 5/02* (2018.01)
*A01H 6/80* (2018.01)

(52) U.S. Cl.
USPC ..... Plt./263.1

(58) Field of Classification Search
USPC ..... Plt./263.1, 373

CPC ... A01H 5/02; A01H 5/12; A01H 5/00; A01H 6/80
See application file for complete search history.

(56) References Cited

PUBLICATIONS

Walters Gardens *Oredenia* 'Fusion of Fire' retrieved on Feb. 8, 2024 at https://www.waltersgardens.com/variety.php?ID=OREFF, 3 pp. (Year: 2024).*

* cited by examiner

*Primary Examiner* — June Hwu

(57) ABSTRACT

A new and distinct x *Oredenia* 'Fusion of Fire' with a dense, low, mounded habit, medium-sized, densely-arranged, deep-green, slightly glossy, rounded, dentate foliage with shallowly palmately lobed margins. The pink flowers are stellate on short heavily-branched panicles over a three-week period beginning in early spring. The foliage develops a bright reddish to light yellow fall color. The new plant is hardy to at least USDA zone 5 and has a medium to fast growth rate.

2 Drawing Sheets

Botanical designation: *Oresitrophe* x *Mukdenia* hybrid (x *Oredenia*).

Cultivar denomination: 'Fusion of Fire'.

BACKGROUND OF THE PLANT

The present invention relates to the new and distinct x *Oredenia* herein also referred to as x *Oredenia* 'Fusion of Fire', by the cultivar name, 'Fusion of Fire', or by the "new plant." The new plant was hybridized by the inventor in May of 2015, at the Gothenburg Botanical Garden. It is an intergeneric cross between a proprietary, unreleased, unnamed selection of *Oresitrophe rupifraga* (not patented) as the female or seed parent and the proprietary unreleased unnamed selection of *Mukdenia rossii* (not patented) as the male or pollen parent. The new hybrid genus is a combination of the two genera used in the cross preceded with an "x" in keeping with international nomenclature standards.

The single seedling represented by x *Oredenia* 'Fusion of Fire' was selected from a group of seedlings made by the inventor, isolated, compared in subsequent years to other *Oresitrophe* and *Mukdenia* plants, and subsequently found to be different from all cultivars known to the inventor, and given the initial breeder code #5 through the evaluation process.

Asexual propagation at the same botanical garden in Gothenburg, Sweden initially by basal cuttings and later by shoot tip sterile tissue culture has shown 'Fusion of Fire' to be stable and reproduce true to type in successive generations since late summer of 2016.

SUMMARY OF THE PLANT

X *Oredenia* 'Fusion of Fire' has not been observed in all possible environmental conditions. The phenotype may vary slightly with changes in environments such as light intensity, fertility, water availability, etc. without any variations in genotype.

'Fusion of Fire' is distinct from all cultivars known to the inventor in the following traits:

1. Dense, low, mounded habit;
2. Large-sized, broad, densely-arranged, deep-green, slightly glossy, rounded, dentate foliage with shallowly palmately lobed margins;
3. Foliage is initially lustrous both adaxial and abaxial becoming matte adaxial;
4. Flowers in densely arranged short panicles of pink;
5. Medium to rapid growth rate;
6. Developing bright reddish to light yellow fall color;
7. Winter hardy to at least USDA zone 5.

Plants of x *Oredenia* 'Fusion of Fire' are distinct but can be compared with the parents. Compared with the selected *Oresitrophe rupifraga* and other forms of the female parent species the new plant has more lobed margins. Compared with the selected form of *Mukdenia rossii* the new plant has larger foliage that is less lobed, better winter hardiness, and denser panicles of pink flowers. The closest known cultivar to 'Fusion of Fire' is x *Mukgenia* 'Flame' (not patented). 'Flame' has much smaller foliage and smaller habit with reddish flowers. The typical fall foliage color of *Mukdenia rossii* is more diverse and more frequently in the yellowish range.

BRIEF DESCRIPTION OF THE DRAWINGS

The color drawings illustrate the overall characteristics of x *Oredenia* 'Fusion of Fire' as a two-year-old plant grown in a partially shaded trial garden with fall color drawings of plants in an unheated greenhouse. The colors are as true as reasonably possible given the technology available. The color values may vary slightly depending on light intensity and quality.

DETAILED BOTANICAL DESCRIPTION

Figure 1:
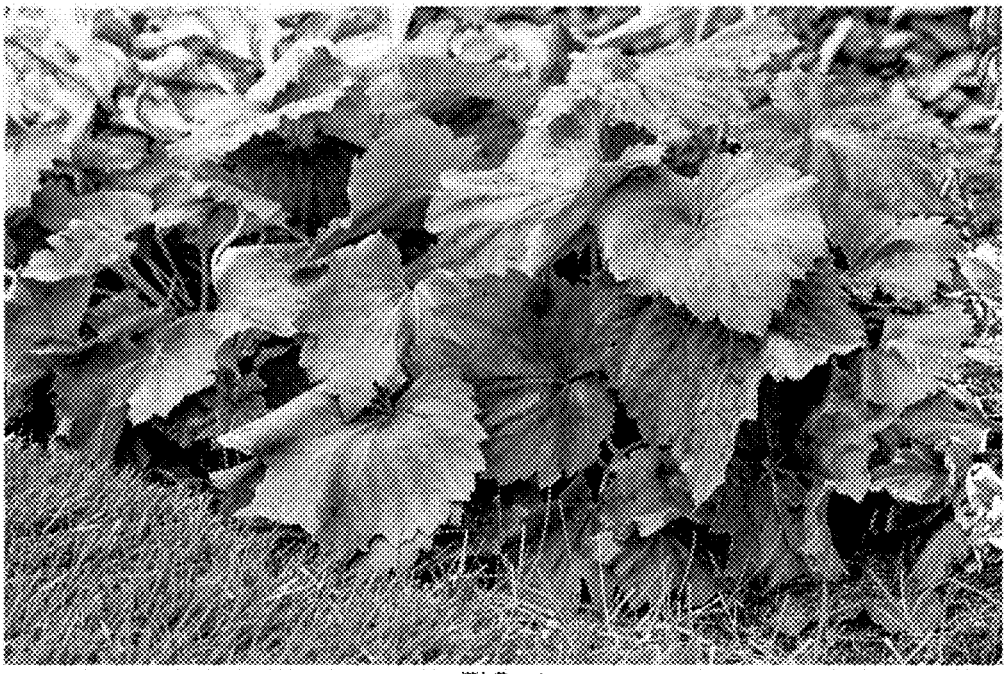
FIG. 1 shows the new plant with summer foliage.
Figure 2:
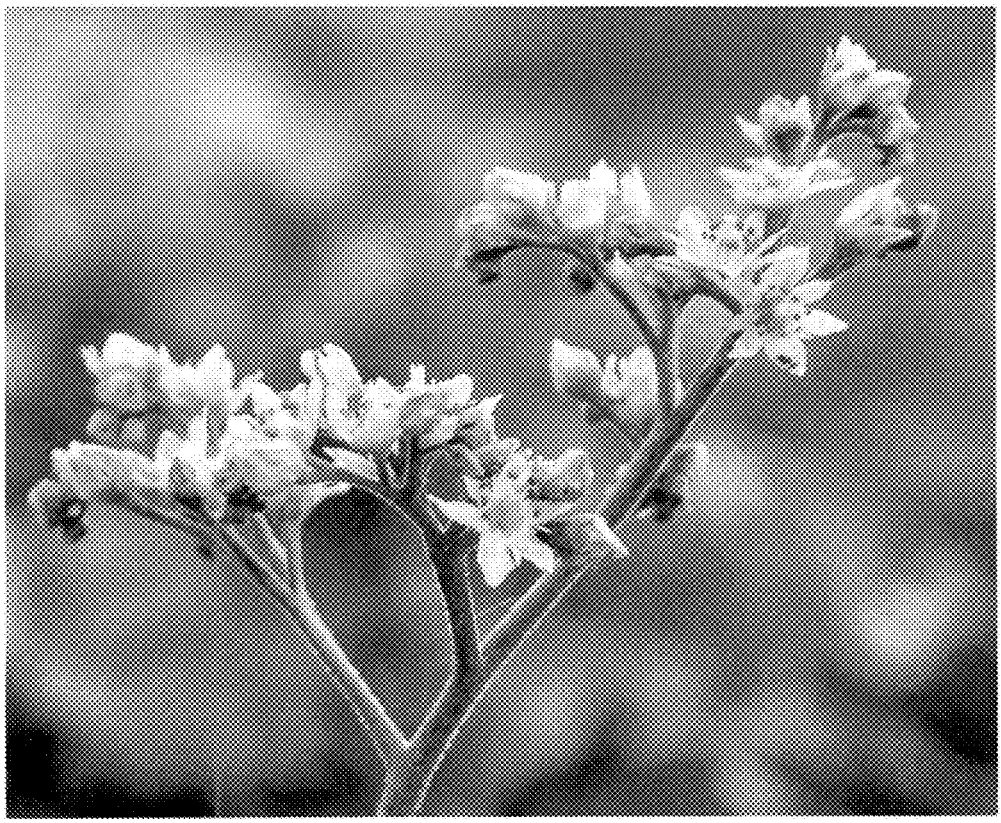
FIG. 2 shows a close-up of the flowers and buds.
Figure 3:
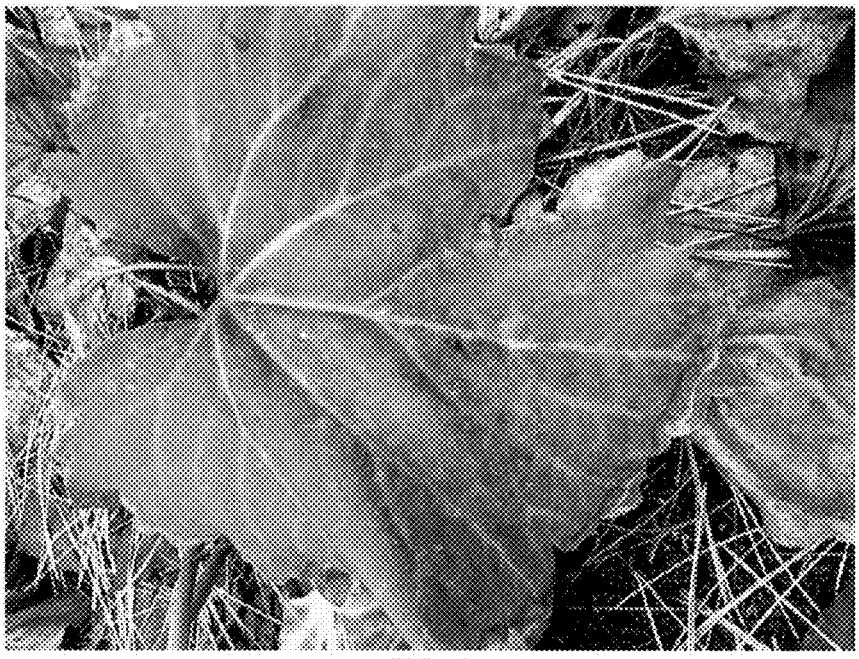
FIG. 3 shows the clump with early fall color.
Figure 4:
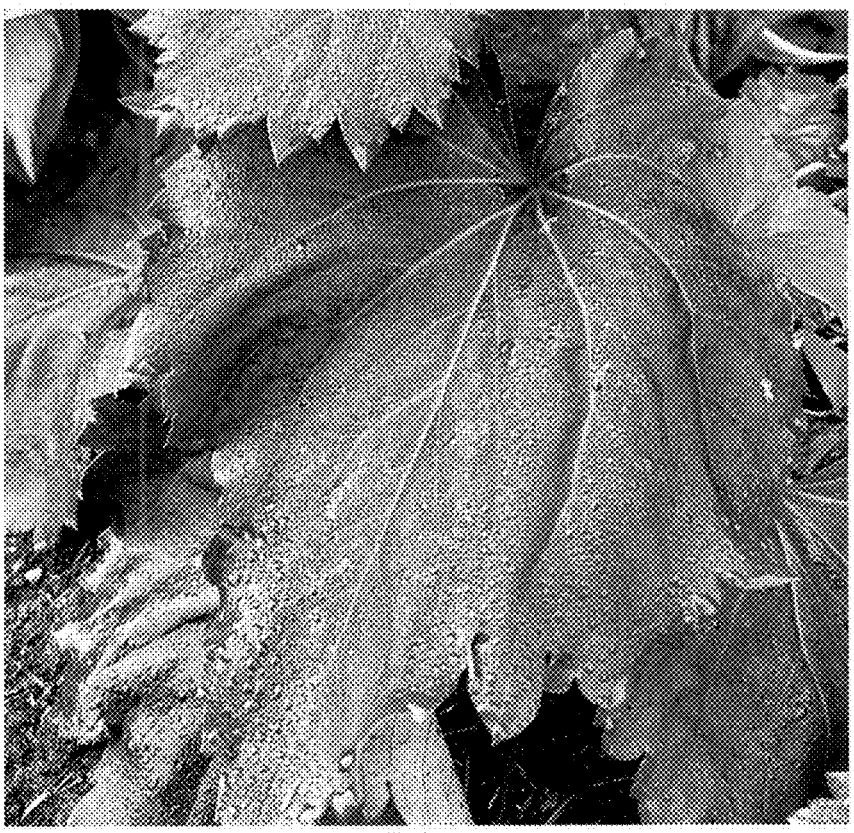
FIG. 4 shows a close-up of the foliage in midsummer.

The following description is based on two-year-old plants growing in a partially shaded greenhouse and in an outdoor partially shaded display garden in Zeeland, MI, USA. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

*Parentage*.—the female parent is a proprietary, unreleased, unnamed selection of *Oresitrophe rupifraga* and the male parent is the proprietary unreleased unnamed selection of *Mukdenia rossii.*

*Asexual propagation*.—division of tissue culture plants, about 15 days to initiate roots; time to finish 25 mm plugs in a one-gallon container about 3 months.

*Growth rate*.—moderate to fast.

*Plant habit*.—low, spreading, herbaceous, evergreen to semi-evergreen foliage, winter-hardy, perennial mound; with heavily branched flower stems; with about 8 to 10 shoots per plant; flowering-size shoots to about 1.5 cm long and about 1.5 cm diameter

*Plant size*.—foliage to about 72 cm wide and about 30 cm tall; flowering to about 45 cm wide and about 19 cm tall.

*Leaves*.—rounded; basal; adaxial and abaxial surface lustrous becoming matte adaxial; rounded apex; cordate base with basal lobes imbricate; margin irregularly shallowly and palmately lobed, and dentate; medium number of indentations; with weak marginal undulations; weak rugosity.

*Leaf size*.—to about 30 cm long and 25 cm wide; lobes to about 3.5 cm long and 4 cm wide; teeth from 1 mm long and 1 mm wide to 3 mm long and 4 mm wide.

*Leaf color*.—young expanding leaves adaxial nearest blend of RHS 138A and RHS 144A and abaxial nearest RHS 147C with a faint blush of nearest RHS 184A; mature leaves adaxial between RHS 139A and RHS NN137A, mature abaxial between RHS 148B and RHS 148C; fall adaxial developing between RHS N57C and RHS 60C, abaxial developing between RHS N170C and RHS 59D; winter dormant.

*Veins*.—palmate; glabrous and smooth adaxial and glabrous and costate abaxial.

*Vein color*.—young adaxial between RHS N144D and RHS 146D, young abaxial nearest RHS 147C; mature adaxial proximally nearest RHS N144A and transitioning distally nearest RHS 138A, abaxial proximally nearest blend between RHS 146D and RHS 145C and distally becoming nearest RHS 146D.

*Petiole*.—glabrous; lustrous; concavo-convex distally, cylindrical in the center portion and proximally becoming applanate; stipulate; size to about 21.5 cm long and about 6 mm diameter at base.

*Petiole color*.—adaxial distally between RHS 138A and RHS 146D, the middle portion between RHS 145B and RHS 146D, proximally nearest RHS 146D and developing a faint blush of nearest RHS 178A; abaxial between RHS 145C and RHS 146D.

*Stipule*.—attached a base of petiole; alate; to about 16 mm long and 25 mm wide including two wings; wings to about 12 mm long and 8 mm wide; wings and apex acute; base truncate.

*Stipule color*.—initially nearest RHS NN155A with distal portion nearest RHS N57C.

*Inflorescence*.—panicle; about 8 to 10 per plant; to about 21 cm long and 4 mm diameter at base; with 4 to 9 branches; flowering portion to about 21 cm tall and 17 cm wide; cylindrical; lustrous; glabrous; attitude semi-upright.

*Peduncle*.—panicle; cylindrical; micro-glandular; size to about 37 cm long and 1 cm diameter.

*Peduncle color*.—variable with less anthocyanin pigment in warmer growing conditions and with less light exposure, proximal portion in cooler conditions with high light nearest RHS 146D, distally nearest RHS 146D with minor to blushing to nearly solid of nearest RHS 178B, in lower light and warmer conditions between RHS 146D and RHS 138A.

*Flower*.—single; perfect; stellate; on terminal branches; about 12 mm across, about 6 mm deep; attitude upright to outwardly.

*Flower fragrance*.—lightly sweet.

*Flowering period*.—beginning early spring, for about 3 weeks; producing up to 52 flowers per branch and up to 230 flowers per panicle.

*Individual flower longevity*.—about 7 days.

*Flower buds one day prior to opening*.—ellipsoidal; acute apex; acute base; about 6 mm long and 4 mm diameter at the center.

*Flower bud color one day prior to opening*.—sepal base between RHS 177D and RHS N170D, distally variable with portions between RHS 62B and 62D and other portions nearest RHS 186D with the distal one-half between RHS 174D and RHS 194A.

*Pedicel*.—cylindrical; glandular; to about 6 mm long and 0.7 mm diameter.

*Pedicel color*.—nearest RHS 148B with a strong blush of nearest RHS 178A.

*Calyx*.—stellate; about 10 mm wide and 4 mm deep, fused in basal 2 mm forming hypanthium 3 mm tall and 3.5 mm diameter.

*Sepals*.—typically, five; lanceolate; narrowly acute apex; truncate base fused in basal 2 mm; margin entire; glabrous except proximal glandular abaxial; slightly lustrous adaxial and abaxial; about 4 mm long and about 1 mm wide at fusion.

*Sepal color*.—adaxial and abaxial between RHS 64A and RHS 70A.

*Petals*.—typically, five in a single whorl, occasionally with up to four additional smaller petals; broadly lanceolate; acute apex; fused in basal 2 mm; margin entire; glabrous adaxial abaxial; to about 7 mm long and 2.5 mm wide at fusion with additional petals up to 7 mm long and 1.5 mm wide.

*Petal color*.—variable depending on temperature; with cooler growing temperatures-when initially open adaxial and abaxial between RHS 69D and RHS 65D, when mature adaxial longitudinal center nearest RHS N57D and margins nearest RHS N155C, abaxial nearest RHS 65D; with warmer growing temperatures-when initially open adaxial between RHS 65D and RHS 65C, abaxial nearest RHS N155B, when mature adaxial and abaxial between RHS N155B and RHS NN155D.

*Androecium*.—variable in number, typically, between six and ten; adnate inner corolla; Filament: cylindrical; lustrous; glabrous; to about 2 mm long and 0.7 mm diameter; color between RHS N155B and RHS NN155C. Anther: oblong ellipsoidal; basifixed; longitudinal; about 1 mm long and 0.7 mm across; color nearest RHS 70A. Pollen: abundant; color between RHS NN155B and RHS NN155C.

*Gynoecium*.—bifid to rarely trifid; about 5.5 mm long. Stigma: bifid; globose; about 0.5 mm diameter; color between RHS NN155B and RHS NN155A. Style: cylindrical; about 3 mm long, 2.5 mm wide, and tapered toward stigma; color proximally nearest RHS 64D distally nearest RHS NN155B. Ovary: partly inferior; 2 mm long and 2.5 mm wide at base; color between RHS 145C and RHS 145D.

*Fruit and seed*.—not observed.

*Growth*.—The new plant is tolerant of winter temperatures from USDA hardiness at least from zones 5 to 8. The new plant grows best with good drainage and adequate moisture and shaded to partially shaded conditions.

*Pests and diseases*.—The new plant is not known to be more or less susceptible or tolerant of diseases and pests that are common to other cultivars or plants in the genera of either *Mukdenia* or *Oresitrophe*.

I claim:

1. A new and distinct variety of x *Oredenia* plant named 'Fusion of Fire' as herein described and illustrated.

* * * * *